Nov. 8, 1932. L. BURBANK Plant Pat. 41
CHERRY
Filed Dec. 3, 1931
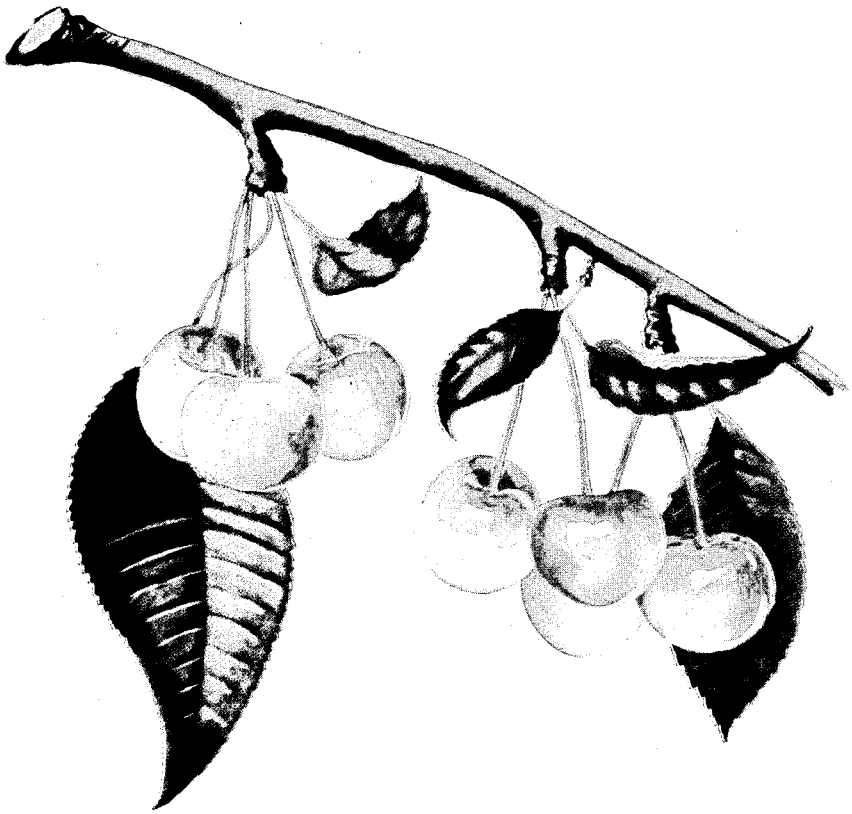
Elizabeth Waters Burbank
Executrix of the estate of
Luther Burbank, deceased
By Robb & Robb
Attorneys Patented Nov. 8, 1932

Plant Pat. 41

UNITED STATES PATENT OFFICE

LUTHER BURBANK, DECEASED, LATE OF SANTA ROSA, CALIFORNIA, BY ELIZABETH WATERS BURBANK, EXECUTRIX, OF SANTA ROSA, CALIFORNIA, ASSIGNOR TO STARK BRO'S NURSERIES & ORCHARDS COMPANY, OF LOUISIANA, MISSOURI

CHERRY

Application filed December 3, 1931. Serial No. 578,833.

This invention relates to a new and distinct variety of cherry. From a commercial standpoint, the new variety is especially valuable owing to the vigorousness of tree growth and toughness and strength of the wood, enabling the branches to carry heavy crops readily without damage to the tree. In addition, the large size of the fruit and the fact that it is not susceptible to cracking or brown rot after rain, as is generally the case in most varieties of cherries, enhances the value and desirability of the new variety.

The prominent distinctions and characteristics of the new variety of cherry which has been asexually reproduced are pointed out and become apparent from the following description and annexed drawing.

*Tree*

*Growth.*—The tree growth is moderately vigorous, the branches being divergent, about 45° from the vertical and generally straight, from which side limbs extend in rather widely spaced relation, making an open tree structure. While the branches are relatively slender, the wood is tough and strong, carrying heavy crops easily. The older bark is roughened by the development of the large lenticels and weathering of the heavy gray scarfskin, the smooth portions being a slate-purple color.

*Lenticels.*—The lenticels are large and rough, generally gray in color but showing light brown under color where broken or rubbed off.

*Scarfskin.*—The scarfskin is heavy and dull gray in color, extending in transverse lines and bands. On smaller branches, this creates a banded or mottled effect, becoming uniform gray on the older twigs.

*Twigs.*—Because of the prominent leaf- and fruit-bud scars, the twigs are very rough and knotty. Terminal bud-scale rings are also very plainly marked. The bark, where smooth, is purple drab in color, largely covered with the light gray scarfskin, and the lenticels small, round, ochraceous tawny (brown), and not very numerous.

*New growth.*—The new growth has rather short to medium internodes, fairly stout, with smooth bark which is slightly glossy. The underside is absinthe green, while the exposed side is shaded with a brownish tinge. Large, prominent axillary buds are produced, russet brown in color, subtended by a distinct shoulder to which the leaf stem is attached. Spur fruit buds are in clusters.

*Petiole.*—The petiole is rather stout, 1 to 1¼ inches long, with a distinct but narrow groove on the upper side. The color generally is absinthe green, modified on the upper side by a strong tinge of vandyke red. The glands are large and prominent, round to elliptical, and distinctly indented, ranging in color from buckthorn brown to ferruginous (reddish brown). The glands are always on the stem and usually ⅛ to ¼ inch from the base of the blade, two in number, and in position from opposite and touching to ⅛ inch distant.

*Mature leaves.*—The mature leaves on new growth vary in size from large to very large, the blade ranging from 3½ to 4½ inches long and 2¼ to 2½ inches wide, long oval or ovate in form, with obtuse to acute base. The margin is rather coarsely double-crenate to nearly serrate. The apex is acute. As seen on the tree, the blade is flat or slightly up-turned at the margin, and the color of the upper surface is Varley's green to forest green (disregarding the luminous character due to transmitted light). The under surface color is modified to light elm green by the surface layer of white cells. The midrib and veins are prominent, attended by faintly brownish pubescence. Scattering minute hairs appear on the entire under surface.

*Flowers.*—The flowers are large and produced in large clusters, well spaced along the twigs. Large petals, circular in outline with obscure stem at insertions on the calyx, are characteristic of the flower, pure white in color. The anthers are small, producing pollen in moderate amount throughout a large portion of the bloom period, some pollen being still discernible after petal fall.

*Fruit*

*Size.*—An important characteristic of the fruit is its size, ranging from large to very large. For a particular tree, the size of the fruit is substantially uniform. On an average the axial diameter is about $\frac{13}{16}$ inch (long), with the greatest transverse diameter about 1 inch (wide) and the shortest transverse diameter about $\frac{13}{16}$ inch (thick).

*Form.*—In shape, the fruit is rounded, blunt cordate, regular, and symmetrical, with a moderately slender stem 1⅜ to 1¾ inches long which is only slightly enlarged at the juncture with the twig, but noticeably enlarged into a collar at the insertion in the cavity of the fruit. The color of the stem is lumiere green. The base of the fruit is very broad with a wide cavity, medium in depth and regular except for the indentation of the suture, of which there is also a suggestion on the opposite side of the cavity. The suture depression is very shallow, practically disappearing over the side of the fruit, the suture becoming merely a fruit line of color, a little more prominent near the apex, and ending abruptly at the pistil scar. The apex is rounded or very slightly indented, with the scar not quite at the median line.

*Surface.*—The surface of the fruit is very smooth and glossy with some dots faintly depressed, while the color of the surface at the lightest areas is light orange yellow, shaded orange pink, with increasing depth of color due to dots and marblings of (pinkish) peach red, shading to nopal red and deep carmine in the most heavily colored portion. The dots are minute and pale orange yellow in color, merging with the general color effect. Owing to the thinness, toughness, and close adherence of the skin, it is only removable from the flesh with some difficulty.

*Flesh.*—The flesh is firm, fibrous, moderately tender and juicy, and only slightly adheres to the pit except at the ventral suture. In color, the flesh is pale ochraceous buff, modified by the whitish radial veinings and faintly pink reflection through the translucent portions from the skin color. Commercially, the fruit would be termed a "white-fleshed" cherry. The juice is colorless, and of but slight sweetness or other flavor unless the flesh is crushed. In flavor, the flesh is mildly sweet, with most of the aroma near the skin.

*Stone.*—The stone is round and almost globular, and is rather small as compared with the size of the fruit, being about $\frac{5}{16}$ inch long, ¼ inch wide, and ¼ inch thick. The ventral suture is broad and heavily ridged while the dorsal suture is a single moderate ridge. The stone is rounded at the base, with the sides slightly uneven, and rounded apex with a minute projecting point. The color of a moist stone is cinnamon buff, while a dry stone is ivory yellow.

*Season.*—In the locality of California, the mature to commercial picking stage is around May 28, while first best quality fruit, ripe for immediate use is about June 8. The last good fruit is obtained about June 20. The fruit hangs well and as has been hereinbefore mentioned, does not crack after rain, nor is it seriously affected by brown rot under these conditions.

In a commercial classification, the cherry hereinbefore described would be placed with the Napoleon, as a firm-fleshed red sweet cherry. There is some resemblance between these varieties, but there are very important distinctions. For example, the foliage of the Napoleon cherry has larger glands, and more often an acuminate apex. Also the fruit is of decided cordate form with rounded apex, and is more compressed than that of the new variety forming the subject matter of this application. The color effect of the fruits are somewhat the same, but the dots are not nearly as numerous and are more submerged in the Napoleon. The axial and longest transverse diameters of the Napoleon cherry are practically equal, which, with the cordate form, gives the fruit a long appearance.

It is to be understood that the foregoing characteristics of the new variety of cherry are typical but subject perhaps to slight variation which may arise by reason of change of environment.

Colors mentioned taken from Ridgeway's Color Standards.

What is claimed is:

A new variety of cherry tree as described characterized by its vigor of growth, the toughness of its wood, and the large size and absence of susceptibility of cracking and rot of its fruit, as shown.

In testimony whereof I affix my signature.

ELIZABETH WATERS BURBANK,
*Executrix of the Estate of Luther Burbank, Deceased.*